US011000361B2

(12) United States Patent
Hong et al.

(10) Patent No.: US 11,000,361 B2
(45) Date of Patent: May 11, 2021

(54) MULTIFOCAL OPHTHALMIC LENS HAVING CHROMATIC ABERRATION CORRECTION

(71) Applicant: Novartis AG, Basel (CH)

(72) Inventors: Xin Hong, Fort Worth, TX (US); Xin Wei, Frisco, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/536,567

(22) Filed: Aug. 9, 2019

(65) Prior Publication Data

US 2019/0358027 A1    Nov. 28, 2019

Related U.S. Application Data

(63) Continuation of application No. 15/498,836, filed on Apr. 27, 2017, now Pat. No. 10,420,638.

(51) Int. Cl.
*A61F 2/16*         (2006.01)
*G02C 7/04*         (2006.01)
*G02C 7/06*         (2006.01)

(52) U.S. Cl.
CPC .......... *A61F 2/1613* (2013.01); *A61F 2/1618* (2013.01); *A61F 2/1637* (2013.01); *A61F 2/1654* (2013.01); *G02C 7/041* (2013.01); *A61F 2/1659* (2013.01); *A61F 2002/1681* (2013.01); *G02C 7/06* (2013.01); *G02C 2202/20* (2013.01); *G02C 2202/22* (2013.01)

(58) Field of Classification Search
CPC .... A61F 2/1613; A61F 2/1618; A61F 2/1637; A61F 2/1654
See application file for complete search history.

(56) References Cited

U.S. PATENT DOCUMENTS

| 5,699,142 | A | 12/1997 | Lee et al. |
| 9,335,564 | B2 | 5/2016 | Choi et al. |
| 10,420,638 | B2 * | 9/2019 | Hong ............... A61F 2/1637 |
| 2009/0088840 | A1 | 4/2009 | Simpson et al. |
| 2013/0229619 | A1 | 9/2013 | Becken et al. |
| 2014/0194986 | A1 | 7/2014 | Zhang et al. |
| 2015/0331253 | A1 | 11/2015 | Choi et al. |

FOREIGN PATENT DOCUMENTS

| EP | 2363097 A1 | 9/2011 |
| EP | 3130314 A1 | 2/2017 |
| WO | 2006068696 A1 | 6/2006 |

\* cited by examiner

*Primary Examiner* — William H Matthews

(57) ABSTRACT

An ophthalmic lens includes an optic comprising an anterior surface, a posterior surface, and an optical axis. At least one of the anterior surface and the posterior surface has a surface profile including a base curvature, a refractive region having the base curvature, and a diffractive region comprising a diffractive profile including a plurality of diffractive steps. At least a portion of the diffractive profile constitutes a combination of a base diffractive profile defining multiple foci for the ophthalmic lens and an achromatizing structure that reduces longitudinal chromatic aberrations.

8 Claims, 7 Drawing Sheets

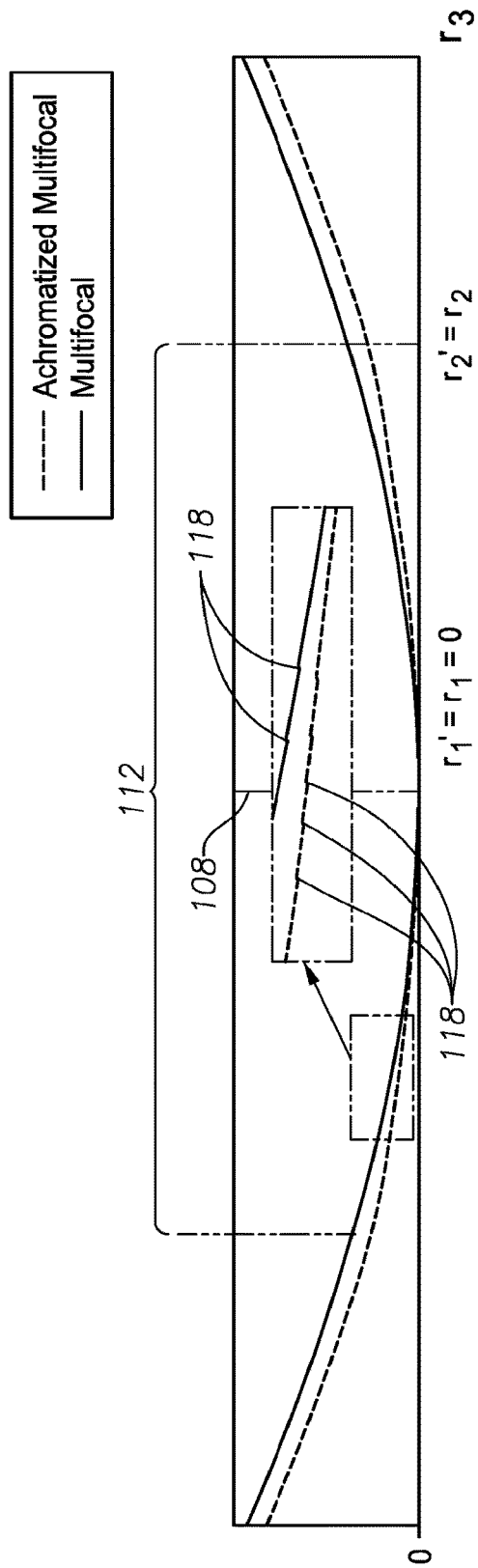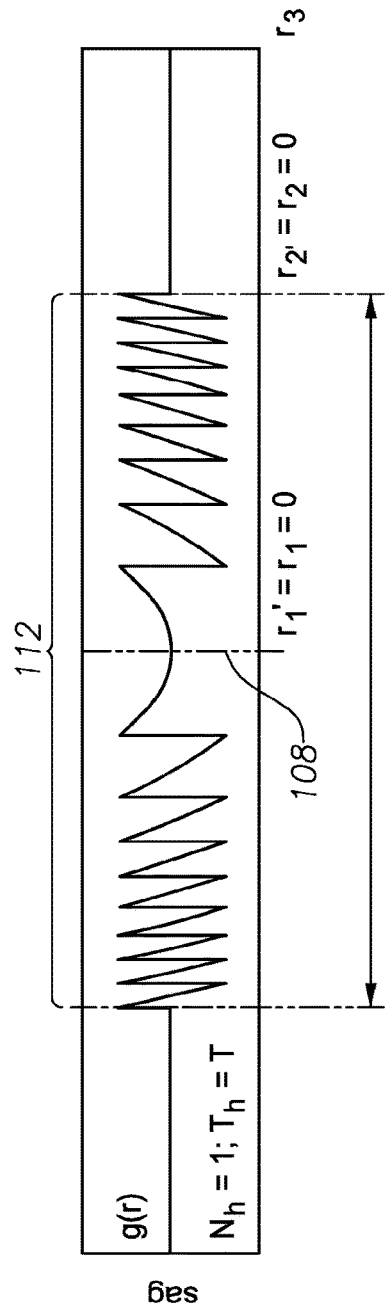
FIG. 3A
FIG. 3B

MULTIFOCAL OPHTHALMIC LENS HAVING CHROMATIC ABERRATION CORRECTION

RELATED APPLICATION

This application is a continuation under 35 U.S.C. § 120 of U.S. application Ser. No. 15/498,836, filed Apr. 27, 2017 and entitled "MULTIFOCAL OPHTHALMIC LENS HAVING CHROMATIC ABERRATION CORRECTION," incorporated herein by reference.

FIELD

This present disclosure relates generally ophthalmic lenses and, more particularly, to ophthalmic lenses having chromatic aberration correction.

BACKGROUND

Intraocular lenses (IOLs) are routinely implanted in patients' eyes during cataract surgery to replace the natural crystalline lens. IOLs may include monofocal IOLs providing a single focus point (e.g., distance vision) and multifocal IOLs providing two or more focus points (e.g., trifocal IOLs providing distance vision, intermediate vision, and near vision). Multifocal IOLs may include diffractive surface profiles, which may include a number of concentric, ring-shaped echelettes that diffract light into several directions simultaneously. Such diffractive surface profiles may provide multiple diffraction orders and focus the light into various images corresponding to different focal lengths of the lens.

Due to the dispersion properties of the lens and the eye, all IOLs (including multifocal IOLs) may exhibit chromatic aberrations where blue light focus in front of the retina and red light focus behind the retina. Such out-of-focus light degrades the lens' overall efficiency in concentrating broadband light energy onto the patient's retina and may impede patients' functional vision (such as low contrast visual acuity under photopic and mesopic conditions at distance). This problem may be particularly bothersome for patients having multifocal IOLs where light is divided among multiple focus points.

Accordingly, there is a need for a multifocal IOL having an optical design that provides chromatic aberration correction.

SUMMARY

The present disclosure generally concerns multifocal ophthalmic lenses (e.g., IOLs) that provide for correction or reduction of chromatic aberrations. More particularly, the present disclosure provides an achromatizing structure that, when added to a diffractive multifocal IOL surface profile, improves white light performance, particularly for distance vision under photopic and mesopic conditions.

In certain embodiments, an ophthalmic lens includes an optic comprising an anterior surface, a posterior surface, and an optical axis. At least one of the anterior surface and the posterior surface has a surface profile including a base curvature, a refractive region having the base curvature, and a diffractive region comprising a diffractive profile including a plurality of diffractive steps. At least a portion of the diffractive profile constitutes a combination of a base diffractive profile defining multiple foci for the ophthalmic lens and an achromatizing structure that reduces longitudinal chromatic aberrations.

In certain embodiments, the present disclosure may provide one or more technical advantages. For example, a multifocal IOL may exhibit chromatic aberrations where blue light focuses in front of the retina and red light focuses behind the retina. These chromatic aberrations may be due, at least in part, to dispersion properties of the IOL itself and/or the eye in which IOL is placed. Out-of-focus light resulting from chromatic aberrations may degrade the overall efficiency of the IOL in concentrating broadband light energy onto the retina and may impede functional vision (e.g., low contrast visual acuity under mesopic conditions at distance). The addition of the achromatizing structure described herein may shorten the distance between blue foci and red foci, which will in turn effectively compress the broadband white light into focus on the retina. Therefore the added achromatizing structure improves broadband white light image quality performance.

In addition to improving broadband white light image quality performance, an achromatizing structure according to certain embodiments of the present disclosure may, when added to a diffractive multifocal IOL surface profile, mitigate a patients' perception of visual disturbances such as halo (i.e., the subjective perception of a bright ring around a light source). In particular, the addition of achromatizing structure to a diffractive profile, as described herein, may reduce the longitudinal chromatic aberration (LCA) of the lens-eye system, and that reduction may lead to the decrease in out-of-focus blur sizes for red and blue lights. Because halos have been associated with the out-of-focus blurs, this reduction in out of focus blurs may result in halo reduction and, potentially, better retinal image contrast.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 3A-3C illustrate an exemplary surface profile of a multifocal IOL having chromatic aberration correction, according to certain embodiments of the present disclosure.

The skilled person in the art will understand that the drawings, described below, are for illustration purposes only. The drawings are not intended to limit the scope of the applicant's disclosure in any way.

DETAILED DESCRIPTION

The present disclosure generally concerns multifocal ophthalmic lenses (e.g., IOLs) that provide chromatic aberration correction. More particularly, the present disclosure provides an achromitizing structure that, when added to a diffractive multifocal IOL surface profile, improves white light performance, particularly for distance vision under mesopic and photopic conditions. In the following description, the lens features providing multifocality and chromatic aberration correction are described in connection with intraocular lenses (IOLs). However, the present disclosure contemplates that those features can also be applied to other ophthalmic lenses, such as contact lenses. As used herein, the term intraocular lens (and its abbreviation IOL) are used to describe lenses that are implanted into the interior of the eye to either replace the eye's natural lens or to otherwise augment vision regardless of whether or not the natural lens is removed.

Figure 1A:
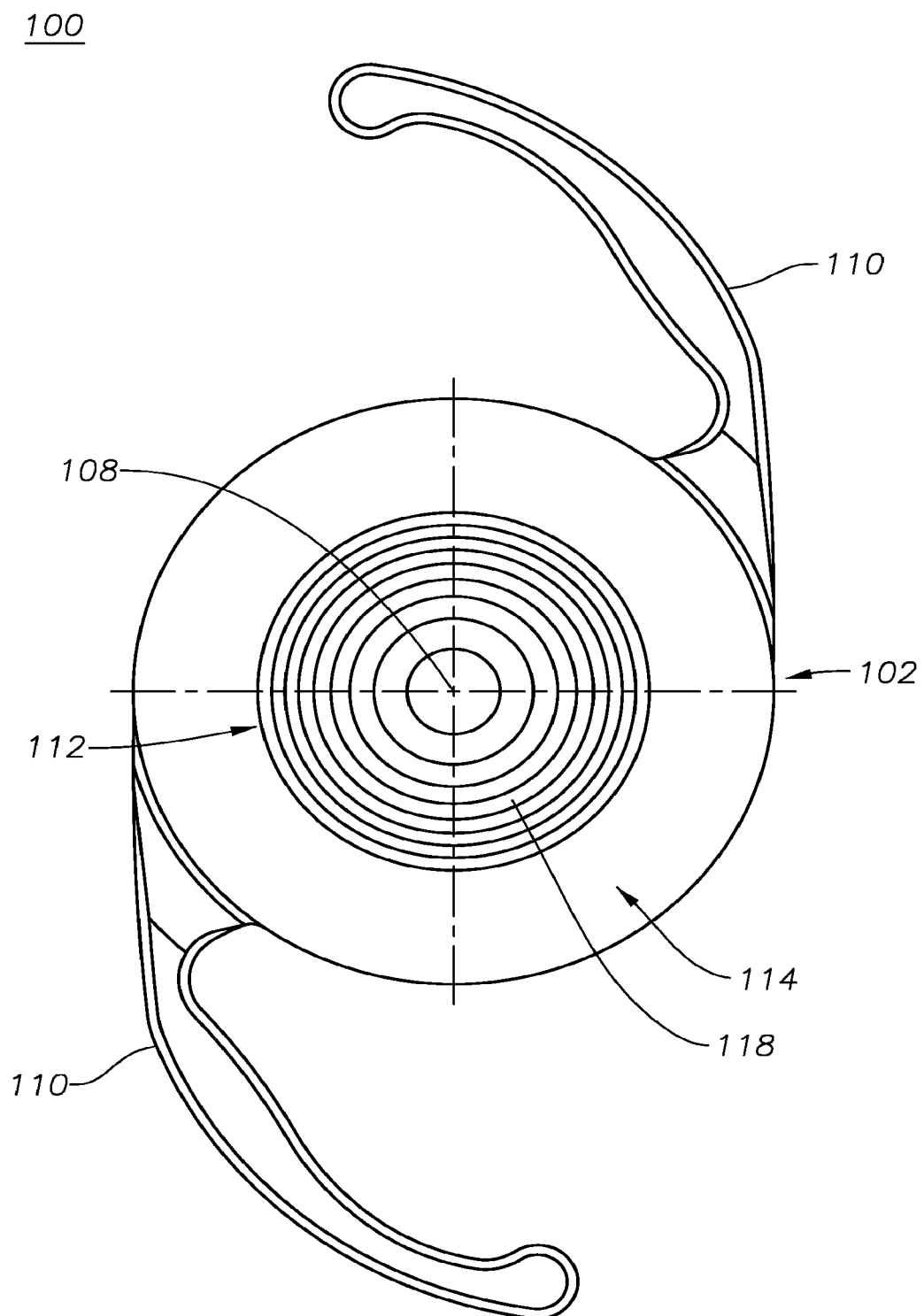
FIGS. 1A-1B illustrate an example embodiment of a multifocal IOL having chromatic aberration correction, according to certain embodiments of the present disclosure.
Figure 1B:
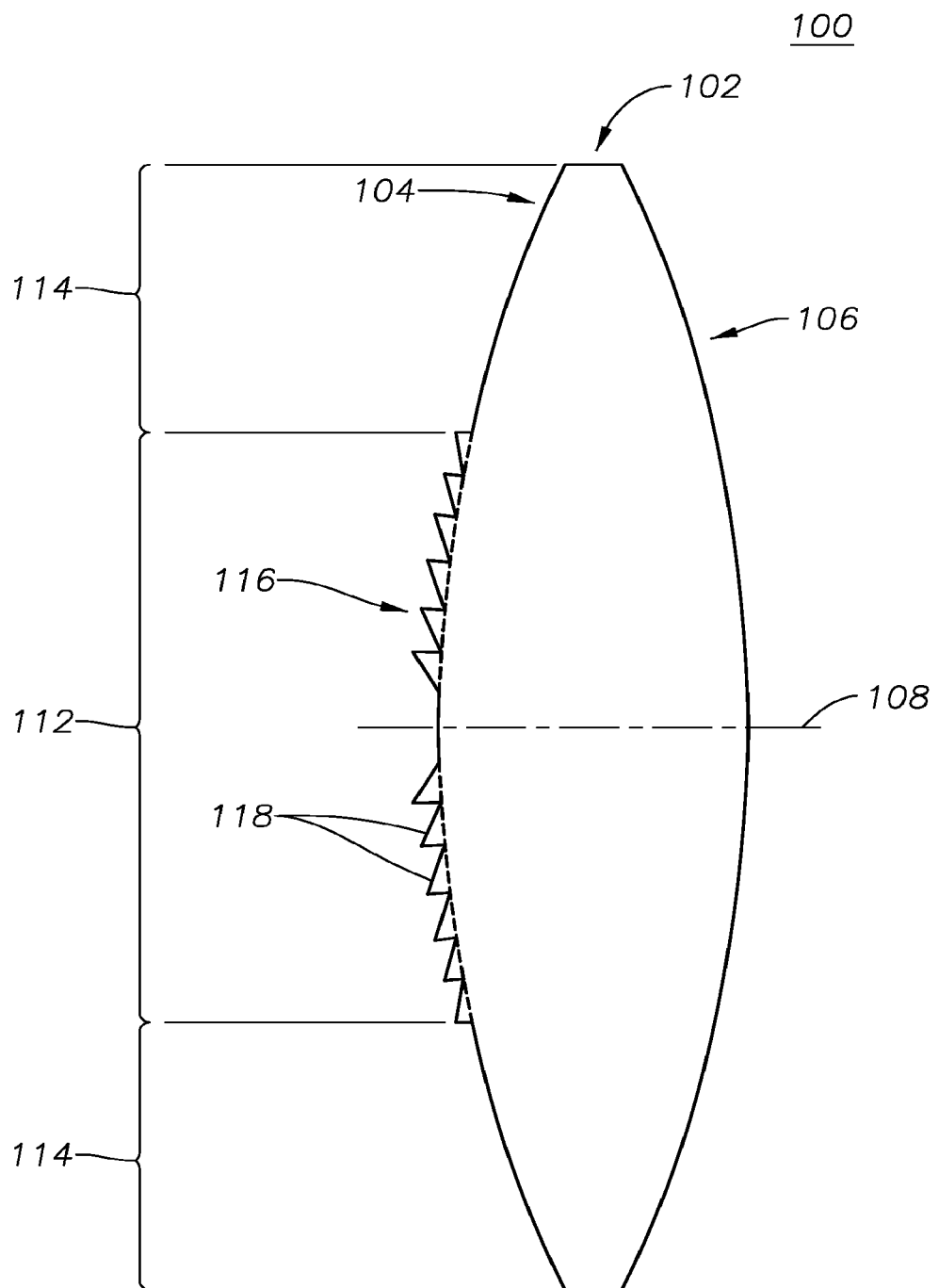

FIGS. 1A-1B illustrate an example embodiment of a multifocal IOL 100 having chromatic aberration correction, according to certain embodiments of the present disclosure. IOL 100 includes an optic 102 having an anterior surface 104 and a posterior surface 106 that are disposed about an optical axis 108. IOL 100 may further include a plurality of haptics 110 generally operable to position and stabilize IOL 100 within the capsular bag of a patient's eye. Although haptics 110 having a particular structure are illustrated for example purposes, the present disclosure contemplates haptics 110 having any suitable structure for stabilizing IOL 100 within the capsular bag, the ciliary sulcus, or any other suitable location within the eye.

In the description below, the anterior surface 104 of optic 102 is described as having a particular surface profile providing multifocality and chromatic aberration correction. However, the present disclosure contemplates that such features may additionally or alternatively be located on posterior surface 106 of optic 102.

The anterior surface 104 of optic 102 may have a base curvature corresponding to a base optical power of the IOL 100. In a multifocal IOL such as IOL 100, the base optical power of IOL 100 typically corresponds to the distance vision of the patient. However, this need not always be the case. For example, a non-dominant eye may have an IOL with a base optical power is slightly less than the corresponding distance power for the patient to improve overall binocular vision for both eyes. In certain embodiments, the base curvature may be aspheric (as described in further detail below).

In addition to a base curvature, the anterior surface 104 of optic 102 may include a plurality of regions. For example, anterior surface 104 may include a diffractive region 112, which may extend from the optical axis 108 to a first radial boundary, and a refractive region 114, which may extend from the first radial boundary to a second radial boundary (e.g., the edge of the optic 102). In certain embodiments, the curvature of diffractive region 112 may be modified relative to the base curvature. Although anterior surface 104 of optic 102 is depicted and described as having only two regions (diffractive region 112 and refractive region 114), the present disclosure contemplates that anterior surface 104 of optic 102 may include a surface profile having any suitable number of regions. As just one example, anterior surface 104 could alternatively include a surface profile having two refractive regions separated by a diffractive region.

In certain embodiments, diffractive region 112 comprises a diffractive structure 116 having a plurality of diffractive steps 118 (also known as zones). Diffractive steps 118 may have a characteristic radial separation to produce constructive interference at characteristic foci. In principle, any diffractive structure 116 that produces constructive interference through phase shifting in interfering zones can be adapted for use in diffractive region 112 to produce a multifocal diffractive ophthalmic lens. Although the diffractive structure 116 of diffractive region 112 is depicted with annular zones, the zones could conceivably be partial, such as semicircular or sectored zones, as well. While the following description will concern a diffractive structure 116 including annular diffractive steps 118, it should be understood by those skilled in the art that suitable substitutions may be made in any embodiment disclosed herein.

At least a portion of the diffractive structure 116 of diffractive region 112 may be characterized, at least in part, as a combination of a base diffractive profile (e.g., $F_{diffractive}$(r, T) of Eq. (4), Eq. (9), and Eq. (11), below) and an achromatizing structure (e.g., g(r) of Eq. (5) and Eq. (11), below). As described in detail below, the addition of the achromatizing structure may provide a multifocal IOL having better white light performance and/or reduced halo as compared to a multifocal IOL not including an added achromatizing structure. To illustrate the difference, the following disclosure first describes an exemplary surface profile not including an added achromatizing structure.

In a multifocal IOL having a diffractive region 112 that does not include the added achromatizing structure described herein, the profile of anterior surface 104 (including both a diffractive region 112 and a refractive region 114) may be defined as follows:

$$Sag(r) = Z_{base}(r) \quad 0 \le r \le r_1$$

$$Sag(r) = Z_{base}(r) + F_{diffractive}(r,T) + \Delta_1 \quad r_1 < r \le r_2$$

$$Sag(r) = Z_{base}(r) + \Delta_2 \quad r_2 < r \le r_3 \qquad \text{Eq. (1)}$$

wherein:
r denotes a radial distance from the optical axis;
$Z_{base}$(r) denotes the base curvature of the surface;
$F_{diffractive}$(r, T) denotes the profile of the diffractive structure 116 that produces multifocality in the design;
T denotes the period in $r^2$ space for the diffractive structure 116;
$r_1$, $r_2$, and $r_3$ denote various radial junction points; and
Δ1 and Δ2 are constants to ensure the appropriate phase shift among different sections of the IOL.

In an embodiment in which diffractive region 112 extends from the optical axis 108 to a first radial boundary and the refractive region 114 extends from the first radial boundary to the edge of the optic 102, $r_1$ may equal zero, $r_2$ may define the first radial boundary, and $r_3$ may define the edge of optic 102.

In embodiments in which the base curvature of anterior surface 104 of optic 102 is aspheric, $Z_{base}$(r) from Eq. (1) may be defined as follows:

$$Z_{base}(r) = \frac{cr^2}{1 + \sqrt{1 - (1+k)c^2 r^2}} + a_2 r^2 + a_4 r^4 + a_6 r^6 + \ldots + a_n r^n \qquad \text{Eq. (2)}$$

wherein,
r denotes a radial distance from the optical axis;
c denotes a base curvature of the surface;
k denotes a conic constant;
$a_2$ is a second order deformation constant;
$a_4$ is a fourth order deformation constant;
$a_6$ is a sixth order deformation constant; and
$a_n$ is a $n^{th}$ order deformation constant, where n may equal any suitable even number (e.g., 20).

Although Eq. (2) is shown above to include out to an $n^{th}$ order deformation constant, the present disclosure contemplates that Eq. (2) may be limited to any suitable number of deformation constants (e.g., only second, fourth, and sixth order deformation constants).

With regard to the diffractive structure $F_{diffractive}(r, T)$ that splits light into different orders that correspond to multiple viewing distances (i.e., diffractive region 112), spacing between neighboring orders may be determined by the period of grating, T (in $r^2$ space, unit: $mm^2$) as follows:

$$\frac{1000}{D_{ADD}} = \frac{T}{2\lambda} \qquad \text{Eq. (3)}$$

wherein, $\lambda$ denotes the design wavelength; and $D_{ADD}$ denotes the spacing between neighboring orders in power space.

The present disclosure contemplates that the diffractive structure $F_{diffractive}(r, T)$ could define any suitable diffractive profile, such as, for example, a bifocal diffractive profile, a trifocal diffractive profile, or an apodized diffractive profile. As one example, diffractive structure $F_{diffractive}(r, T)$ can be expressed as follows:

$$F_{diffractive}(r, T) = 0 \qquad \text{Eq. (4)}$$
$$r_1 \le r < r_{12}$$
$$F_{diffractive}(r, T) = h_{diffractive} \times \left( \frac{(r - r_{12})^2}{T} - \left\lfloor \frac{(r - r_{12})^2}{T} \right\rfloor \right)$$
$$r_{12} \le r \le r_2$$

wherein, r denotes a radial distance from the optical axis, $r_1$, $r_{12}$, and $r_2$ denote various radial junction points (where $r_1$ and $r_2$ are the same from Eq. (1), above);

T denotes the period in $r^2$ space for the diffractive structure 116

$\lfloor \ \rfloor$ denotes floor function where $\lfloor x \rfloor = \max\{m \in z | m \le x\}$ is the set of integers; and $h_{diffractive}$ denotes a step height of a multifocal diffractive lens.

As another example, multifocal diffractive structure $F_{diffractive}(r, T)$ can define an apodized bifocal diffractive structure such as that described in U.S. Pat. No. 5,699,142, the contents of which is hereby incorporated by reference.

Figure 2A:
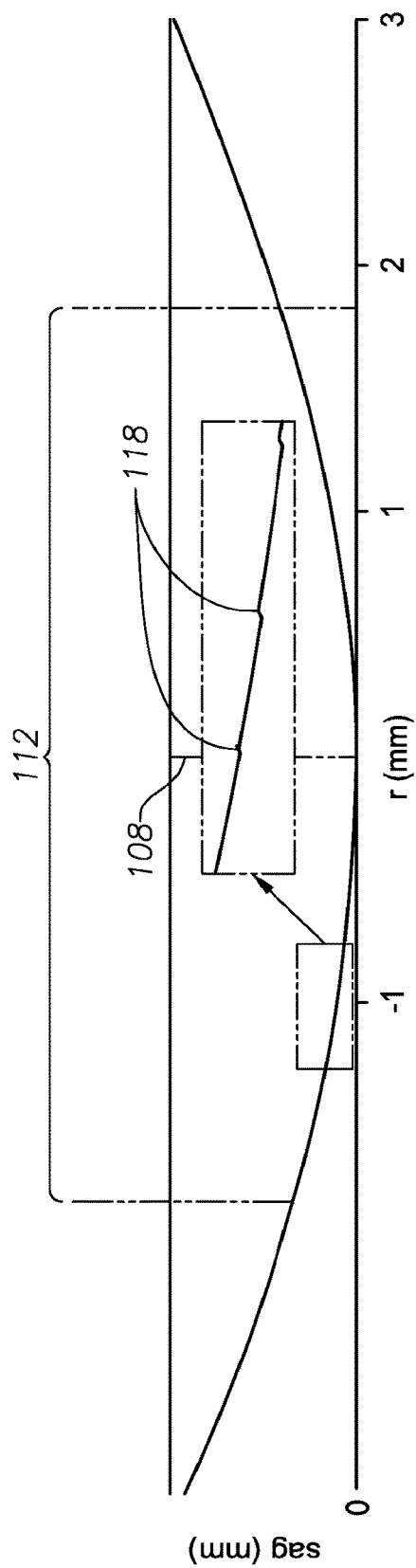
FIGS. 2A-2B illustrate an exemplary surface profile of a multifocal IOL having a diffractive region that does not include an added achromatizing structure.
Figure 2B:
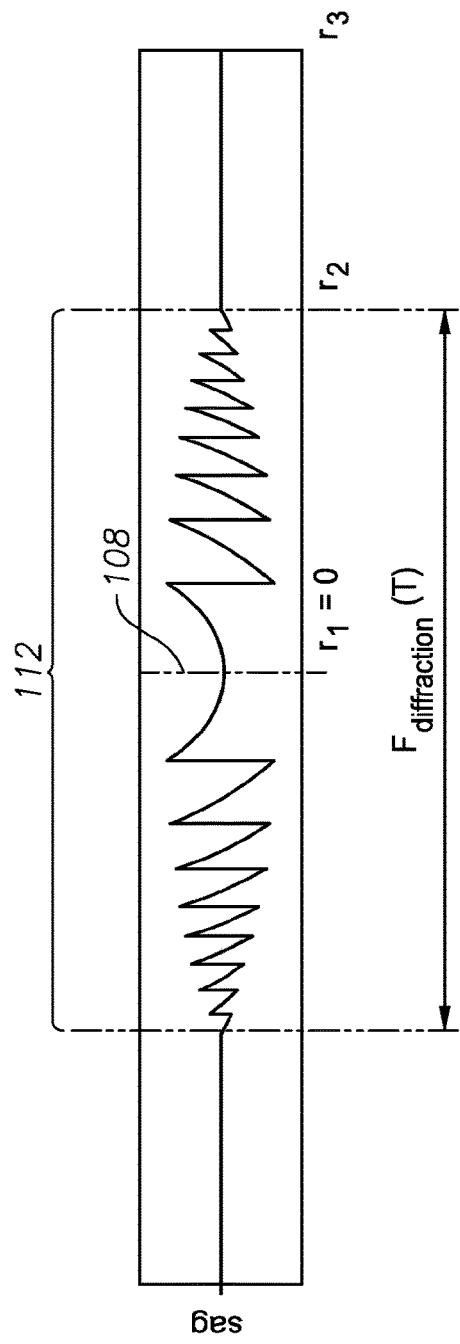

As yet another example, multifocal diffractive structure $F_{diffractive}(r, T)$ can define an trifocal diffractive structure such as that described in U.S. Pat. No. 9,335,564, the contents of which is hereby incorporated by reference FIGS. 2A-2B illustrate the surface profile of a multifocal IOL having a diffractive region 112 that does not include the added achromatizing structure described herein (designed according to Eqs. (1)-(3)). In particular, FIG. 2A depicts a plot of sag (in mm) versus radius (in mm), including diffractive steps 118 in diffractive region 112. To better illustrate the diffractive steps 118, FIG. 2B is a plot of the same surface profile depicted in FIG. 2A but showing only the effect of the added $F_{diffractive}(r, T)$. In the depicted example, $F_{diffractive}(r, T)$ defines an apodized bifocal diffractive structure in which the step height of the diffractive grating is decreased with increased radial distance from the optical axis 108.

Due to at least in part to dispersion properties of the IOL itself and/or the eye in which IOL may be placed, a multifocal IOL designed according to above Eqs. (1)-(3) (an example of which is depicted in FIGS. 2A-2B) may exhibit chromatic aberrations where blue light focuses in front of the retina and red light focuses behind the retina. Such out-of-focus light may degrade the overall efficiency of the IOL in concentrating broadband light energy onto the retina and may impede functional vision (e.g., low contrast visual acuity under mesopic conditions at distance).

Accordingly, in certain embodiments, the above-described multifocal IOL may be modified to further include an achromatizing structure added to the surface profile to generate the multifocal IOL 100 having chromatic aberration correction. Stated differently, at least a portion of the diffractive structure 116 of diffractive region 112 may be characterized, at least in part, as a combination of a base diffractive profile and an achromatizing structure such that the optic 102 (including diffractive region 112 and refractive region 114) generates multiple foci and exhibits reduced chromatic aberrations. The achromatizing structure may include any suitable diffractive structure that, when added to a base diffractive structure of a diffractive region of a multifocal IOL, reduces the magnitude of longitudinal chromatic aberrations as compared to a multifocal IOL having a diffractive region including only the base diffractive structure.

An exemplary achromatizing structure can be expressed as follows:

$$g(r) = 0 \qquad \text{Eq. (5)}$$
$$0 \le r \le r_1'$$
$$g(r) = h \times \left( \frac{r^2}{T_g} - \left\lfloor \frac{r^2}{T_g} \right\rfloor \right)$$
$$r_1' < r \le r_2'$$
$$g(r) = 0$$
$$r_2' < r \le r_3$$

wherein, r denotes a radial distance from the optical axis, $r_1'$, $r_2'$, and $r_3$ denote various radial junction points (where $r_3$ is the same from Eq. (1), above);

$T_g$ denotes the period in $r^2$ space of the added achromatizing structure;

$\lfloor \ \rfloor$ denotes floor function where $\lfloor x \rfloor = \max\{m \in z | m \le x\}$ is a set of integers; and h denotes a step height.

In certain embodiments, $r_1'$ of Eq. (5) may equal $r_1$ of Eq. (1) (which may equal zero, as discussed above) and $r_2'$ of Eq. (5) may equal $r_2$ of Eq. (1) (which may define the location of the first radial boundary separating the diffractive region 112 and refractive region 114, as discussed above). In certain other embodiments, $r_1'$ of Eq. (5) may not equal $r_1$ of Eq. (1) and $r_2'$ of Eq. (5) may not equal $r_2$ of Eq. (1). In such embodiments, $r_1'$ of Eq. (5) may greater than $r_1$ of Eq. (1) and $r_2'$ of Eq. (5) may be less than $r_2$ of Eq. (1).

The step height h in Eq. (5) may correspond to integral number of wavelengths as follows:

$$h = \frac{N_h \lambda}{(n_{IOL} - n_{ocularmedia})} \qquad \text{Eq. (6)}$$

wherein, $N_h$ is an integral (in certain embodiment, $N_h$ may be ½ for the 1st diffractive region);

λ denotes the design wavelength;

$n_{IOL}$ denotes refractive index of IOL; and $n_{ocularmedia}$ denotes refractive index of surrounding ocular media such as aqueous or vitreous.

In certain embodiments, the period $T_g$ in Eq. (5) may be the same as the multifocal grating period T of Eq. (1). In certain other embodiments, the period $T_g$ can may be constrained by a relationship as follows:

$$T_g = NT$$

or $$T = NT_g \qquad \text{Eq. (7)}$$

wherein,

N is an integral;

T denotes the period in $r^2$ space of the original multi focal grating structure in Eq. (1);

$T_g$ denotes the period in $r^2$ space of the added achromatizing structure.

The added achromatizing structure defined by Eq. (5) may shift light to other orders relative to the standard diffractive grating included in Eq. (1). This will change the focal distance of the multifocal design by:

$$\Delta f = \frac{N_h T_g}{2\lambda} \qquad \text{Eq. (8)}$$

wherein,

λ denotes the design wavelength;

Δf denotes the spacing between the shifted diffractive order and the original order;

$N_h$ is the integral associated with step height in Eq. (6);

To compensate for such defocus shift, the corresponding segment of base curve may be adjusted as follows:

$$Sag(r) = Z_{base}(r) \quad 0 \le r \le r_1$$

$$Sag(r) = Z_{base}(r) + F_{diffractive}(r,T) + \Delta_1' \quad r < r \le r_1'$$

$$Sag(r) = Z'_{base}(r) + F_{diffractive}(r,T) + \Delta_1'' \quad r_1' < r \le r_2'$$

$$Sag(r) = Z_{base}(r) + F_{diffractive}(r,T) + \Delta_1''' \quad r_2' < r \le r_2$$

$$Sag(r) = Z_{base}(r) + \Delta_2 \quad r_2 < r \le r_3 \qquad \text{Eq. (9)}$$

wherein:

r denotes a radial distance from the optical axis, $Z_{base}(r)$ denotes the base curvature that corrects for patients distance vision as shown in Eq. (2);

$Z'_{base}(r)$ denotes the base curvature that corrects for patients distance vision and takes into account of the focus shift caused by addition of achromatizing structure in Eq. (5);

$F_{diffractive}$ (r, T) denotes the base diffractive profile that provides multifocality in the design;

T denotes the period in $r^2$ space for the base diffractive profile;

$r_1$, $r_2$, and $r_3$ denote junction points at the surface, as shown in Eq. (1);

$r_1'$ and $r_2'$ denote junction points at the surface, as shown in Eq. (5)

$\Delta_1'$, $\Delta_1''$, $\Delta_1'''$, and $\Delta_2'$ are constants to ensure the appropriate phase shift among different sections of the IOLs.

The $Z'_{base}(r)$ in Eq. (9) can be further expressed as an aspheric surface as follows:

$$Z'_{base}(r) = \frac{c'r^2}{1 + \sqrt{1-(1+k')c'^2 r^2}} + a_2' r^2 + a_4' r^4 + a_6' r^6 + \ldots + a_n' r^n \qquad \text{Eq. (10)}$$

wherein, r denotes a radial distance from the optical axis;

c' denotes a base curvature of the surface;

k' denotes a conic constant;

$a_2'$ is a second order deformation constant;

$a_4'$ is a fourth order deformation constant;

$a_6'$ is a sixth order deformation constant; and $a_n'$ is a $n^{th}$ order deformation constant, where n may equal any suitable even number (e.g., 20).

Although Eq. (10) is shown above to include out to an $n^{th}$ order deformation constant, the present disclosure contemplates that Eq. (10) may be limited to at most $20^{th}$ order deformation constants.

In certain embodiments, one or more of the parameters of Eq. (10) (c'. k', $a_2'$, $a_4'$, $a_6'$, ..., $a_n'$) are adjusted relative to the parameters of Eq. (2) (c. k, $a_2$, $a_4$, $a_6$, ..., $a_n$) in order to compensate for the defocus shift Δf as outlined in Eq. (8).

A surface profile of the anterior surface 104 of the IOL 100 having chromatic aberration correction (due to the added achromatizing structure) that improves broadband white light performance may be achieved by combining Eq. (5) and Eq. (9) (or, in the alternative, Eq. (1)) as follows:

$$Sag_{achromatized\_multifocal} = Sag(r) + g(r) \qquad \text{Eq. (11)}$$

Figure 3C:
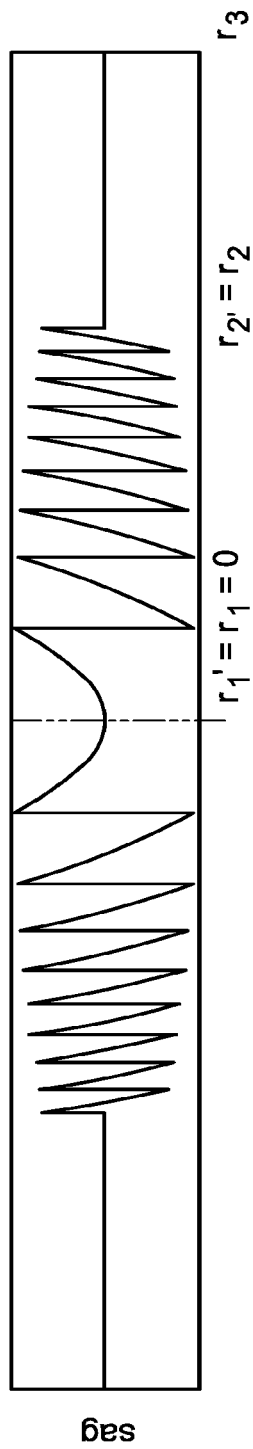
Figure 4A:
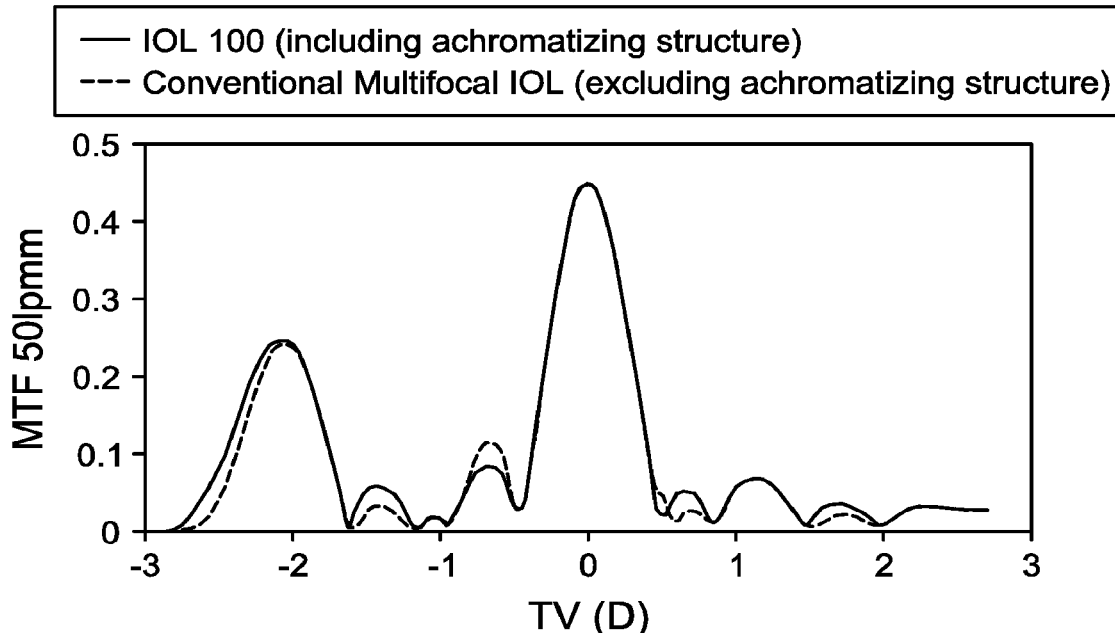
FIGS. 4A-4D are MTF plots illustrating both white light and green light performance of an exemplary IOL like that depicted in FIG. 1 (including the achromatizing structure described herein) as compared to a multifocal IOL excluding the achromatizing structure described herein for both large and small apertures.
Figure 4B:
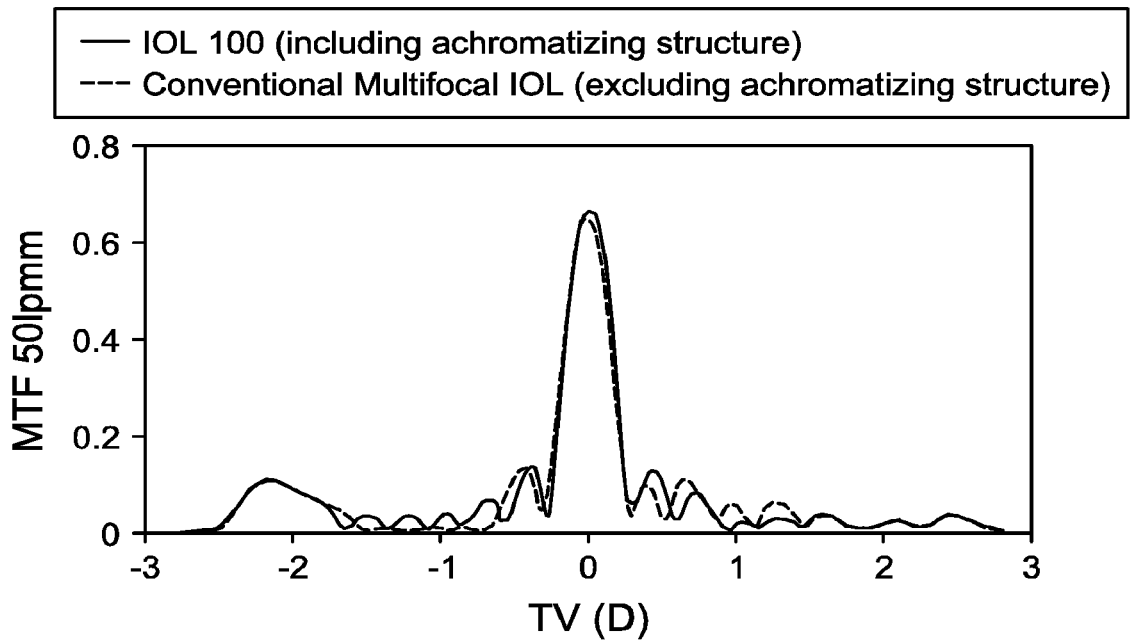
Figure 4C:
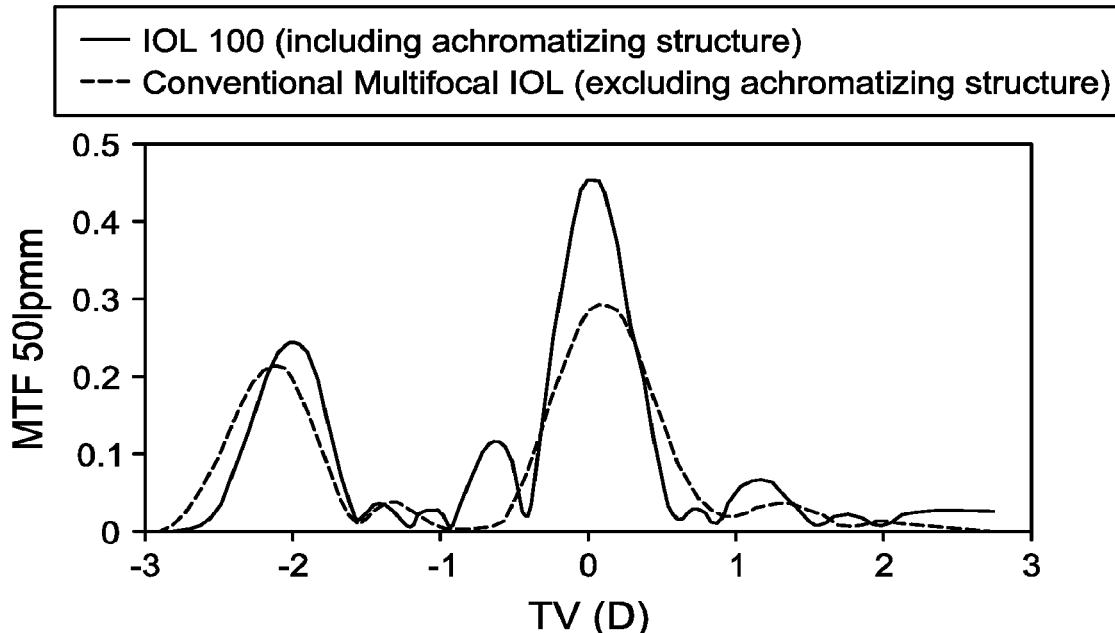
Figure 4D:
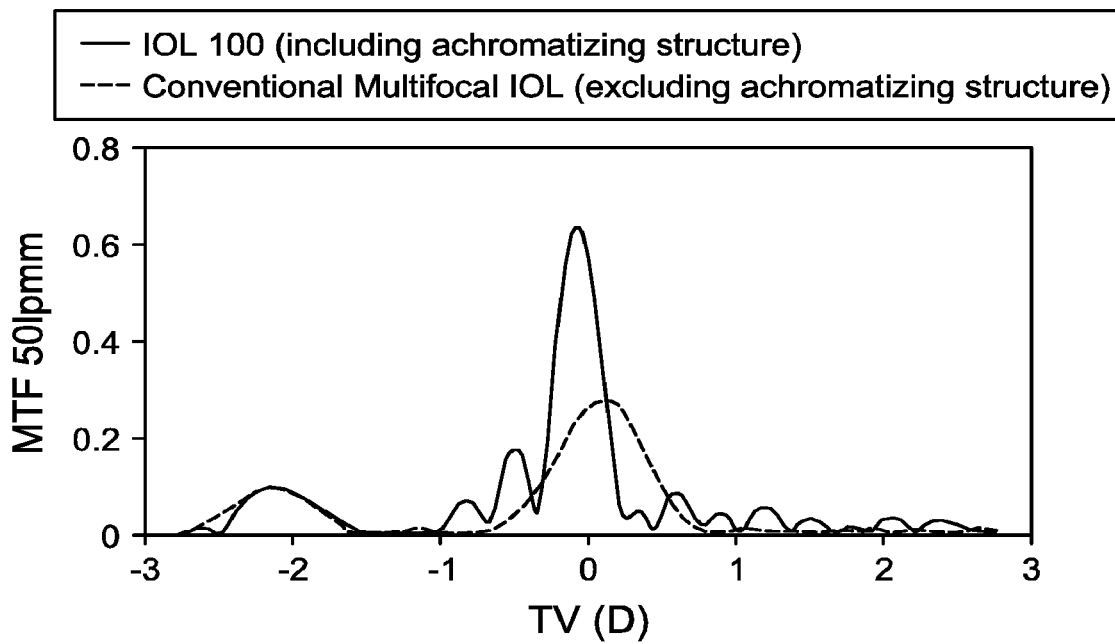

FIGS. 3A-3C illustrate the surface profile a multifocal IOL 100 having chromatic aberration correction (designed according to Eq. (11)), according to certain embodiments of the present disclosure. In particular, FIG. 3A depicts a plot of sag (in mm) versus radius (in mm) of an exemplary achromatized multifocal IOL 100 including modified diffractive steps 118 resulting from the addition of the above-described achromatizing structure. Also plotted is the surface profile not including the achromatizing structure (the same profile depicted in FIG. 2A). By comparing the two, it can be seen that the addition of the achromatizing structure results in more pronounced diffractive steps 118. Also, the result of the compensation for defocus shift (see Eq. (9) and corresponding description above) can be seen as a decrease in sag in diffractive region 112 of the achromatized multifocal surface profile. FIG. 3B is a plot showing only the added achromatizing structure g(r) defined in Eq. (5), while FIG. 3C is a plot of the same achromatized multifocal surface profile depicted in FIG. 3A but showing only the effect of the summed $F_{diffractive}$(r, T) and g(r).

As discussed above, a multifocal IOL designed according to Eqs. (1)-(3) (an example surface profile for which is depicted in FIGS. 2A-2B) may exhibit longitudinal chromatic aberration (LCA) due to the dispersion of eye and the IOL material, In other words, blue light may focus in front of the retina and red light may focus behind the retina. LCA of such a multifocal IOL may be characterized as follows:

$$LCA = \frac{1}{f_{blue}} - \frac{1}{f_{red}} \qquad \text{Eq. (12)}$$

wherein, $f_{blue}$ denotes the focal length of the pesudophakic eye under blue wavelength (e.g. 400 nm); and $f_{red}$ denotes the focal length of the pesudophakic eye under red wavelength (e.g. 700 nm)

When a multifocal design is modified via Eq. (11) to include the achromatizing structure described herein, the added achromatizing structure will reduce the LCA as follows:

$$\Delta LCA = \frac{2\lambda_{blue}}{N_h T_g} - \frac{2\lambda_{red}}{N_h T_g} \quad \text{Eq. (13)}$$

In particular, as the wavelength of blue light is smaller than the wavelength of the red light, the added structure g(r) always yields negative ΔLCA. In other words, the added structure will shorten the distance between blue foci and red foci. This will in turn effectively compress the broadband white light into focus on the retina. Therefore the added achromatizing structure improves broadband white light image quality performance.

Eq. (13) can also be rewritten as follows:

$$N_h T_g = \frac{2(\lambda_{blue} - \lambda_{red})}{\Delta LCA} \quad \text{Eq. (14)}$$

This means given LCA correction (ΔLCA), Eq. (14) may dictate how $N_h T_g$ should be selected.

FIGS. 4A-4D are modulation transfer function (MTF) plots illustrating both white light and green light performance of an exemplary IOL 100 (including the achromatizing structure described herein) as compared to a multifocal IOL excluding the achromatizing structure for both large and small apertures. As is illustrated, IOL 100 provides increased white light performance for both large and small apertures while substantially maintaining green light performance for both large and small apertures.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic lens, comprising an optic comprising an anterior surface, a posterior surface, and an optical axis, at least one of the anterior surface and the posterior surface having a surface profile including:
 a base curvature;
 a refractive region having the base curvature;
 a diffractive region comprising a diffractive profile comprising a plurality of diffractive steps, at least a portion of the diffractive profile being a combination of:
  a base diffractive profile defining multiple foci for the ophthalmic lens; and
  an achromatizing structure that reduces longitudinal chromatic aberrations; and the surface profile is defined as follows:

$$Sag_{achromatized\_multifocal} = Sag(r) + g(r);$$

$g(r) = 0$ $0 \leq r \leq r_1';$ $g(r) = h \times \left( \frac{r^2}{T_g} - \left\lfloor \frac{r^2}{T_g} \right\rfloor \right)$ $r_1' \leq r \leq r_2';$ $g(r) = 0$ $r_2' \leq r \leq r_3;$ wherein:
 Sag(r) defines the surface profile of the ophthalmic lens excluding the achromatizing structure;
 g(r) defines the achromatizing structure;
 $r_3$, $r_1'$, $r_2'$ denote junction points on the surface profile;
 $T_g$ denotes a period in $r^2$ space of the achromatizing structure;
 $\lfloor \ \rfloor$ denotes floor function where $\lfloor x \rfloor = \max\{m \in z | m \leq x\}$ is the set of integers; and
 h denotes a step height.

2. The ophthalmic lens of claim 1, wherein the base curvature corresponds to a base optical power of the ophthalmic lens.

3. The ophthalmic lens of claim 1, wherein:
the diffractive region extends from the optical axis to a first radial boundary; and
the refractive region extends from the first radial boundary to an edge of the optic.

4. The ophthalmic lens of claim 1, wherein the base diffractive profile comprises an apodized diffractive profile.

5. The ophthalmic lens of claim 1, wherein n defines an outer edge of the optic.

6. The ophthalmic lens of claim 1, wherein:

$$Z_{base}(r) = \frac{cr^2}{1 + \sqrt{1 - (1+k)c^2 r^2}} + a_2 r^2 + a_4 r^4 + a_6 r^6 + \ldots + a_n r^n;$$

$Z_{base}(r)$ denotes the base curvature;
r is a radial distance from the optical axis;
c is a base curvature of the surface;
k is a conic constant; and
$a_2$, $a_4$, $a_6$, and $a_n$ are, respectively, second, fourth, sixth, and $n^{th}$ order coefficients,
 where n is an even number.

7. The ophthalmic lens of claim 6, wherein n=20.

8. The ophthalmic lens of claim 1, wherein:
$h = N_h \lambda / (n_{IOL} - n_{ocularmedia})$;
$N_h$ is an integral;
λ denotes the design wavelength;
$n_{IOL}$ denotes refractive index of IOL; and
$n_{ocularmedia}$ denotes a refractive index of an ocular media of a patient.

* * * * *